(12) United States Patent
Yun

(10) Patent No.: US 9,844,458 B2
(45) Date of Patent: Dec. 19, 2017

(54) CONDOM HAVING IMPROVED FUNCTIONALITY

(71) Applicant: Heecheol Yun, Incheon (KR)

(72) Inventor: Heecheol Yun, Incheon (KR)

(*) Notice: Subject to any disclaimer, the term of this patent is extended or adjusted under 35 U.S.C. 154(b) by 387 days.

(21) Appl. No.: 14/641,504

(22) Filed: Mar. 9, 2015

(65) Prior Publication Data
US 2015/0173939 A1    Jun. 25, 2015

Related U.S. Application Data

(63) Continuation-in-part of application No. PCT/KR2013/002415, filed on Mar. 22, 2013.

(51) Int. Cl.
*A61F 6/04* (2006.01)
*A61F 6/00* (2006.01)

(52) U.S. Cl.
CPC .............. *A61F 6/04* (2013.01); *A61F 6/005* (2013.01); *A61F 2006/048* (2013.01)

(58) Field of Classification Search
CPC .. A61F 6/18; A61F 6/144; A61F 6/148; A61F 6/142; A61F 6/04; A61F 6/005; A61F 2006/048; A61F 2006/047; A61F 6/00; A61F 6/065; A61B 5/06
See application file for complete search history.

(56) References Cited

U.S. PATENT DOCUMENTS

| 4,852,586 A | 8/1989 | Haines | |
| 5,209,242 A * | 5/1993 | Shields | ...................... A61F 6/04 |
| | | | 128/842 |
| 5,623,946 A * | 4/1997 | Hessel | ................... A61F 6/065 |
| | | | 128/844 |
| 2005/0076917 A1* | 4/2005 | Wray | ........................ A61F 6/04 |
| | | | 128/844 |

(Continued)

FOREIGN PATENT DOCUMENTS

| EP | 1949876 A1 | 7/2008 |
| KR | 20-1988-0000390 U | 2/1988 |
| KR | 20-0356020 Y1 | 7/2004 |

(Continued)

OTHER PUBLICATIONS

International Search Report for PCT/KR2013/002415 dated Dec. 18, 2013 from Korean Intellectual Property Office.

*Primary Examiner* — Ophelia A Hawthorne
(74) *Attorney, Agent, or Firm* — Park & Associates IP Law, P. C.

(57) ABSTRACT

A condom is configured to include a space such that a front glans part of the condom does not excessively come into contact with the penis of a man by selecting a material having moderate elasticity such as soft synthetic resin or synthetic latex rubber or a foamed rubber material conforming thereto or the like for the front part of the condom made from a soft rubber material; and includes embossed sponge layers or fine soft hairs additionally laminated on the inside and outside of the condom, to provide an excellent mois- (Continued)

turizing effect such that an excellent contraceptive effect and a sexual pleasure-increasing effect can be simultaneously obtained when a user wears the condom, thereby providing multiple effects such as contributing to the treatment of patients with chronic dyspareunia or patients with anorgasmia and the like.

2 Claims, 5 Drawing Sheets

(56) References Cited

U.S. PATENT DOCUMENTS

2007/0277833 A1 12/2007 Ou
2014/0090650 A1* 4/2014 Brunner .................... A61F 6/04
128/844

FOREIGN PATENT DOCUMENTS

KR 10-2007-0116533 A 12/2007
KR 10-0848234 B1 7/2008

* cited by examiner

CONDOM HAVING IMPROVED FUNCTIONALITY

CROSS REFERENCE TO PRIOR APPLICATION

This application is a continuation-in-part (CIP) Application of PCT International Patent Application No. PCT/KR2013/002415 filed on Mar. 22, 2013, which is hereby incorporated by reference in its entirety.

BACKGROUND

The present invention has been devised for the purpose of avoiding personal or social criticism and waste due to undesired pregnancy by improving a structure of male condom and thus further encouraging the public use of the condom and of further enhancing a functionality of the condom by providing a woman with a sexual anesthesia treating effect and a man with an effect of prevention of impotence, premature ejaculation etc. by mixing a suitable amount of vasodilators with jelly liquid for package of the condom and thus increasing sexual pleasure in the use of the condom.

For a structure of the condom generally used up to now, a main body part of the condom is mainly made of natural latex or artificial latex material having excellent flexibility and elasticity as can be seen in FIG. 5 or patent document 1 of prior art(Korean Registered Utility Model No. 20-0356020), and a constricting ring—which is circular elastic body or annular ring body and the like—is provided at a rear inlet, and lubricant jelly is applied on both inner and outer surfaces of the condom and then the condom is individually packed and thereafter distributed as a product.

However, such a conventional condom has problems that its surface consists of only simple smooth surface and thus the jelly tends to be dried in the use of the condom, and in particular, when secreting liquid of a female partner side is insufficient, surface lubrication is insufficient and thus friction force increases, accordingly, the female partner suffers significant vaginal pain, and in a sever case, a slight damage of vaginal wall may be caused.

Induction of the vaginal wall pain due to such insufficiency of lubricity reduces an original primary contraception function of the condom and thus makes the use of the condom avoided.

In addition, when the conventional generally-used condom is worn, a penis of the man and an inner surface of the condom completely closely contact with each other; therefore, the sexual pleasure effect felt by the male partner considerably decreases, which also makes the man avoid the use of the condom.

The present invention aims at providing a new structure of the condom which fundamentally eliminates the structural defect that both of the male and female partners suffer and thus, for the man, avoids the reduction of sexual pleasure due to excessively close contact with the condom and for the woman, fundamentally avoids disease damage or reduction of sexual pleasure due to the drying of the vaginal secreting liquid and the friction.

SUMMARY

In view of the background art described above, the present invention has an object of obtaining a lubricant moisturizing and sexual pleasure improvement effect resulting from a frictional force reduction effect of condom itself by widely and largely forming a front glans penis portion of the condom and also adding uneven spongy layer having a good elasticity or soft fine hairs(downy hairs or very minute and soft hairs) to inner and outer surfaces of the condom for improving a common structure of a condom made of soft rubber film material whose inner and outer surfaces consist of only simple smooth surface, and an objects of ensuring the above-mentioned various functionalities by substituting jelly liquid for a package of the condom with a functional jelly liquid having an effect of enlarging the blood vessels and thus promoting the circulation of the blood over the entire surface of the vaginal wall in sexual intercourse while ensuring lubricity of the jelly liquid in the use of the condom.

To achieve the above objects, the present invention can simultaneously achieve both excellent contraception effect and sexual pleasure improvement effect in the use of the condom by forming a space so that a front glans penis portion of the condom does not excessively closely contact with the male penis and additionally laminating, as moisturizing means having an excellent moisturizing effect, uneven spongy layers or fine hairs made of suitable elastic material such as soft synthetic resin or synthetic latex rubber and similar foamed rubber material and the like, on inner and outer surfaces of conventional condom made of soft rubber material.

Furthermore, the present invention can induce appropriate enlargement of peripheral blood vessels distributed in a contact portion between the female vagina and male penis in the use of the condom to significantly enhance the sexual pleasure in the use of the condom by mixing a suitable amount of vasodilators widely used as anti-impotence drug such as Viagra with the jelly liquid provided inside a package of the condom.

The condom of the present invention has the following functional effects:

Since the surface of the condom has the uneven spongy layers or fine hairs having a good moisturizing effect, the lubricant of the condom or female vaginal secreting liquid is not easily dried in the use of the condom is worn, and thus the sexual intercourse itself is smoothly done and the sexual pleasure is significantly enhanced.

Since the uneven spongy layer or fine hairs having a good flexibility and elasticity is selectively doubly formed on the entire surface of the condom, the man or woman can feel very good sexual pleasure and thus easily reach the orgasm, which is also helpful to sound and healthy sexual life.

The moisturizing effect and sexual pleasure enhancement effect promote the secretion of the female vaginal liquid, thereby contributing to treating patients with dyspareunia or sexual anesthesia.

In the case of the man, since the condom does not excessively closely contact with a front portion of the penis and a certain space is formed, the touch felt by the glans penis in the use of the condom is keen as if the penis directly contacts with the vagina, whereby a conventional disadvantage is avoided that the sexual pleasure is reduced in the use of the condom.

By mixing a suitable amount of the vasodilators with the jelly liquid accommodated in a package of the condom, capillaries in a contact portion between the vagina and penis are locally enlarged in the use of the condom, thereby significantly increasing the sexual pleasure, and accordingly, an effect is obtained that female disease such as sexual anesthesia, colpoxerosis and dyspareunia can be effectively prevented and treated and male urological disease such as impotence, premature ejaculation, reduction of sexual pleasure etc. can be also treated, while reliable contraceptive function is exhibited, and in particular, a positive effect can be expected that the phenomenon of avoiding the condom is changed to preference of the use of the condom, therefore, the present invention can be said to be a very useful invention.

DETAILED DESCRIPTION

Figure 7:
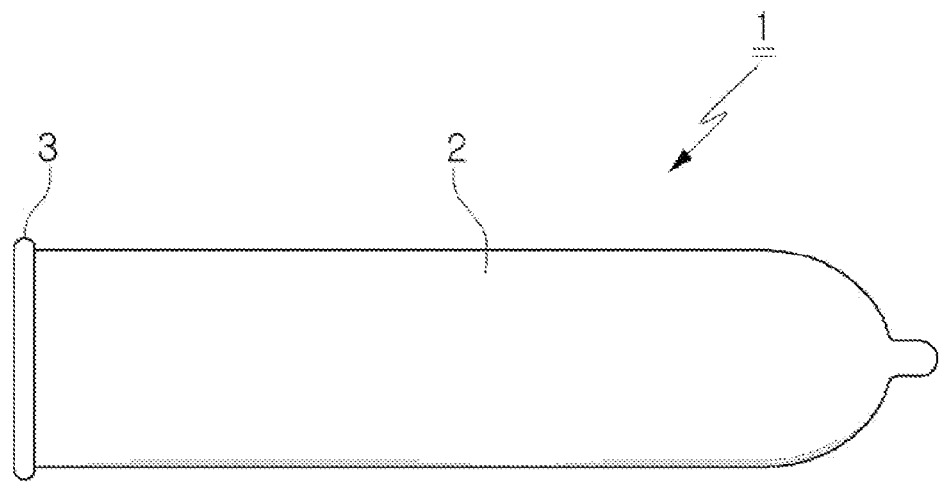
FIG. 7 is a view illustrating an example of conventional condom generally used.

In a case of a conventional condom (1) generally used up to now, a main body (2) is made of material such as natural latex or soft synthetic rubber and the like, and a constricting ring (3) is formed at a rear inlet, as illustrated in FIG. 7. Such an existing condom (1) has a surface part consisting of simple smooth surface.

The present invention is intended to improve a functionality of such an existing condom (1) by internally and externally coating moisturizing means (S) which holds a large quantity of lubricant applied to the condom (1) and thus has a moisturizing function as illustrated in FIGS. 1 to 5.

The condom (1) of the present invention is made of soft material such as natural latex or synthetic rubber etc. by a known method, with a constricting ring (3) provided at a rear portion of main body (2). In the present invention, a front glans penis portion (A) of the condom (1) is widely and largely formed so that a certain space (6) sufficiently remains inside the front glans penis portion in order that the male glans penis is spaced apart from an inner surface of the front glans penis portion of the condom (1) even while the male glans penis is inserted and erected in the front glans penis portion of the condom.

Figure 1:
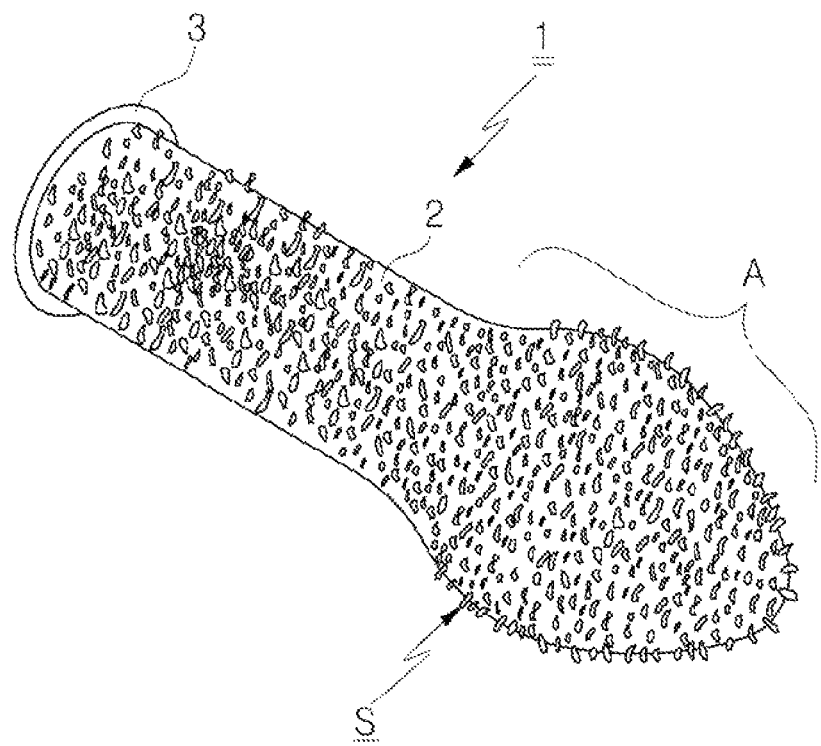
FIG. 1 is a perspective view illustrating a preferred embodiment of a condom of the present invention.
Figure 2:
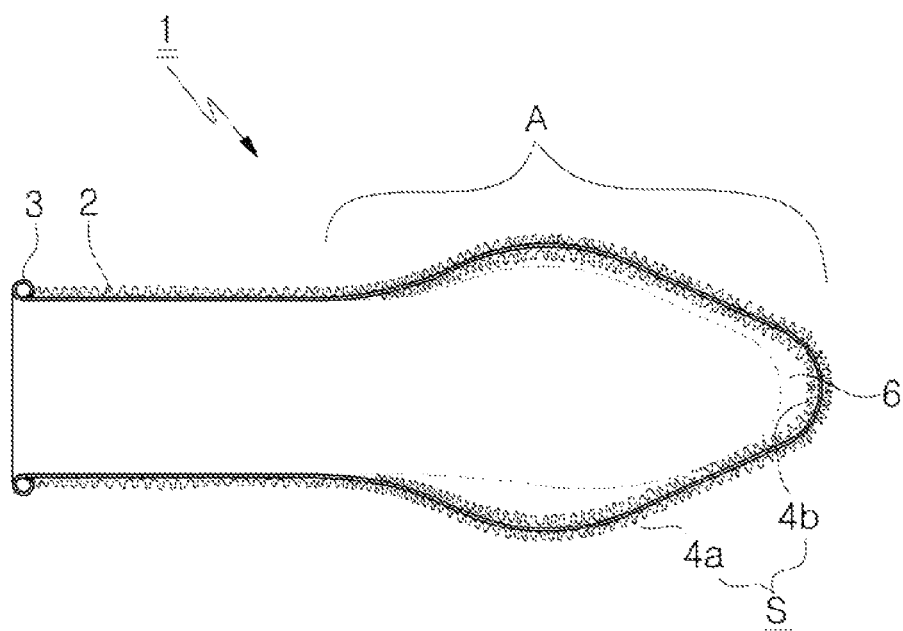
FIG. 2 is a cross-sectional view of the condom of the present invention.
Figure 3:
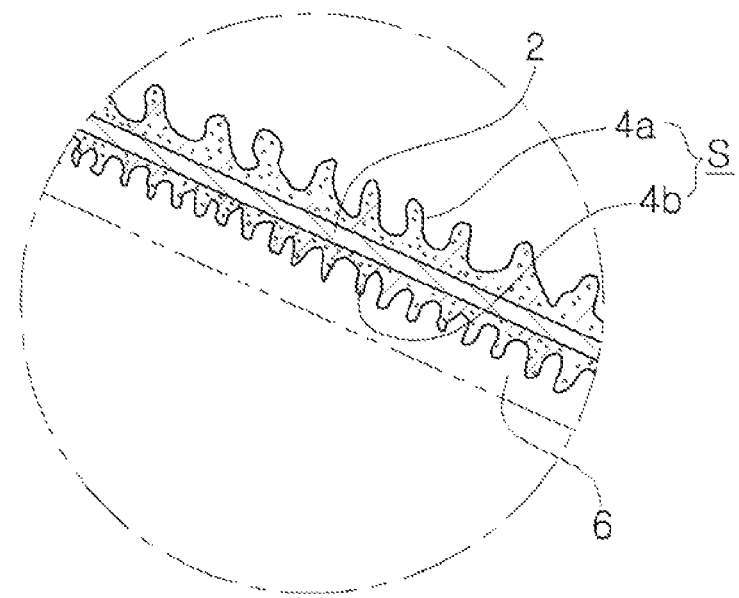
FIG. 3 is a partially enlarged cross-sectional view of FIG. 2.
Figure 4:
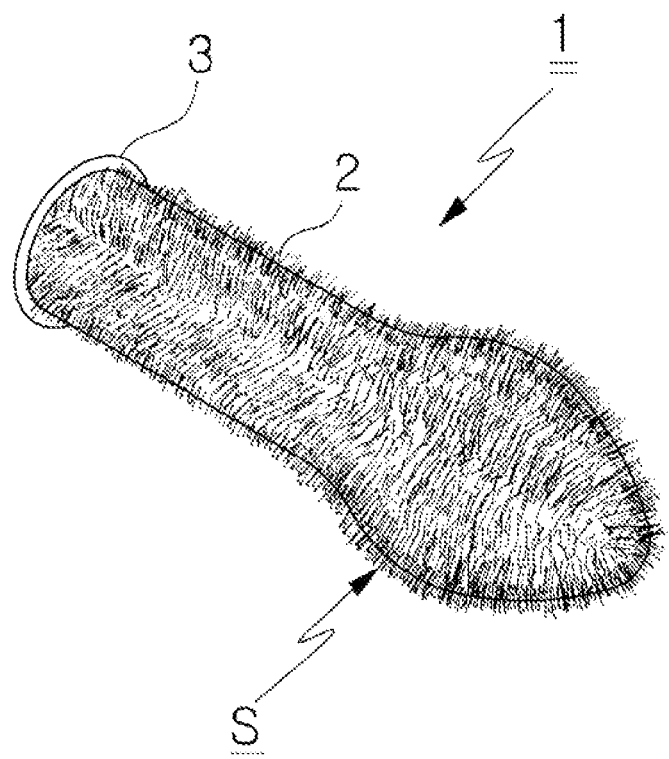
FIG. 4 is a exemplary view where fine hairs are applied as moisturizing means of the present invention.
Figure 5:
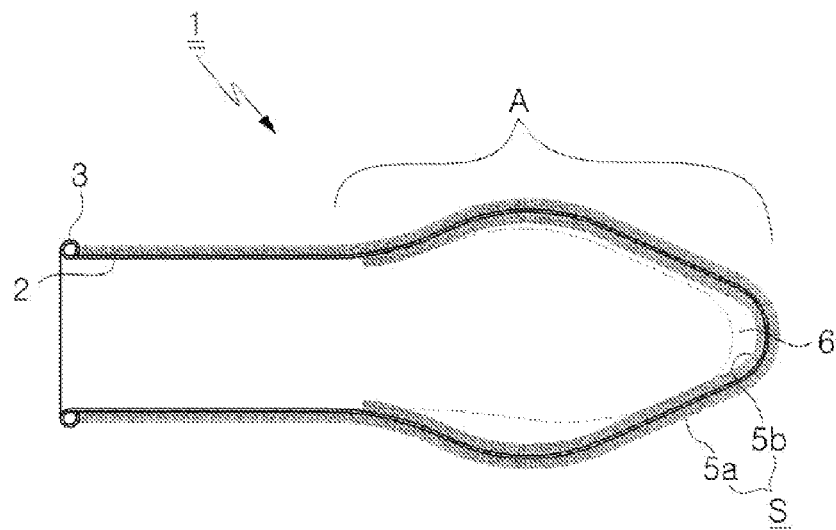
FIG. 5 is a cross-sectional view of FIG. 4.

As the moisturizing means (S) formed on the inner and outer surfaces of the condom (1) by coating, uneven spongy layers (4a, 4b) of the same material as the main body (2) are formed on the inner and outer surfaces of the condom (1) by coating as illustrated in FIGS. 1 to 3, or soft fine hairs (5a, 5b) of the same material as the main body (2) are formed on the inner and outer surfaces of the condom (1) by coating as illustrated in FIGS. 4 and 5.

The uneven spongy layers (4a, 4b) or fine hairs (5a, 5b) are produced from natural latex or synthetic rubber unharmful to a human body. It is preferable that the uneven spongy layers (4a, 4b) are formed with a porous structure by finely foaming the material. Alternatively, the uneven spongy layers (4a, 4b) is made in the form of sheet and then adhered to the entire outer surface of the condom (1) or inner surface of the frond glans penis portion (A) of the condom (1).

Figure 6:
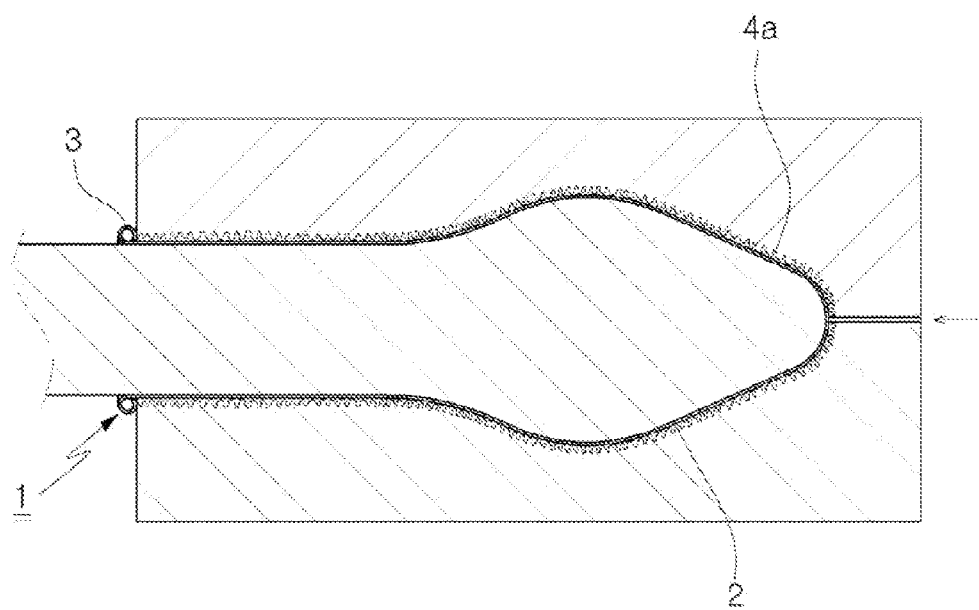
FIG. 6 is a view showing an embodiment of manufacturing process of the present invention.

The uneven spongy layers (4a, 4b) may be integrally adhered by separately preparing injection molds and injecting foam resin to the entire outer surface of the condom (1) or the inner surface of the front glans penis portion (A) of the condom (1) in an insert molding manner as illustrated in FIG. 6. The injection structure in FIG. 6 illustrates an example where the uneven spongy layer (4a) is coated on the entire outer surface of the condom (1) coupled with a core. Although not illustrated, when the uneven spongy layer (4b) is to be coated on the inner surface of the glans penis portion (A), the uneven spongy layer (4a) is coated on the outer surface of the condom (1) as illustrated in FIG. 6 and then is hardened, and thereafter is turned inside out and then coupled with the core, and thereafter the injection is performed in the insert molding manner.

Furthermore, the spongy layers (4a, 4b) having irregular uneven structure may be coated on the outer or inner surface of the condom (1) according to another method by spraying resin liquid onto the surface (spray depositing method).

The uneven spongy layers (4a, 4b) is formed of the same material as the main body (2) of the condom (1) or similar material. Surfaces of the spongy layers (4a, 4b) consist of spongy structure that is a fine porous structure, and the fine hairs (5a, 5b) are also produced from the same material as the main body (2) of the condom (1) or similar material and are densely formed, and therefore, have a good moisturizing effect of holding the lubricant applied to the condom (1) or female secreting liquid in the use of the condom and exhibit soft touch.

Therefore, when the condom (1) is worn, the outer uneven spongy layer (4a) or outer fine hairs (5a) on the outer surface of the main body (2) imparts lubricant friction effect and thus very soft touch when rubbing against the female vaginal wall, and serves to adequately enhance the sexual pleasure depending on the use of the condom.

In addition, the uneven spongy layer (4a) has an excellent moisturizing effect due to its own porous structure, and the fine hairs (5a) have an excellent moisturizing effect due to its dense structure. Therefore, the uneven spongy layer and hairs have an effect that the vaginal secreting liquid is maximally prevented from being dried and the damage of the vaginal wall or the induction of pain is prevented.

Furthermore, the certain space (6) remains inside the front glans penis portion (A) of the main body (2) of the condom without the front glans penis portion closely contacting with the erected male glans penis, and thus the inner uneven spongy layer (4b) or inner fine hairs (5b) formed on the inner surface of the glans penis portion (A) generates irregular friction on the male erected glans penis to continuously impart sexual stimulation to the glans penis where peripheral nerves are concentrated. Therefore, even with the condom (1) worn, the male user can feel a good sexual pleasure as if his penis directly rubs against the vaginal wall.

Such an operational effect obtained by the configuration of the condom (1) according to the present invention can greatly contribute to increasing the sexual pleasure for the man as well as woman. Such sexual pleasure-increasing effect and the moisturizing effect of the lubricant and female secreting liquid have a functional effect that a phenomenon of avoiding the use of the conventional condom (1) can be fundamentally eliminated. Furthermore, the condom of the present invention can be widely used as an original contraceptive device for preventing undesired pregnancy, and an additional effect of healing the dyspareunia or sexual anesthesia etc. can be simultaneously obtained as a user prefers the use of the condom (1) thanks to the sexual pleasure-increasing effect.

Figure 8:
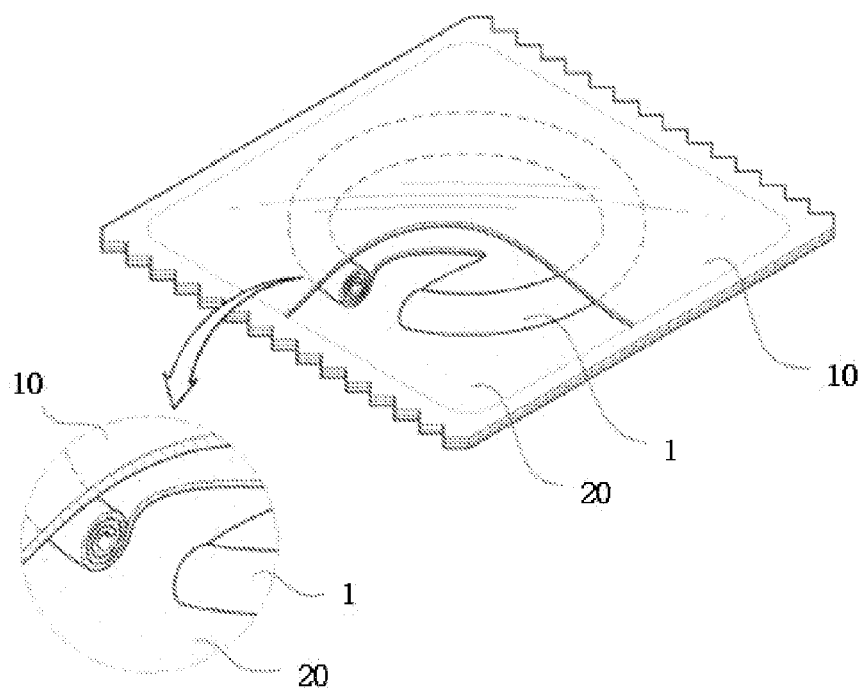
FIG. 8 illustrates a state where the condom of the present invention is packed in a package.
Figure 9:
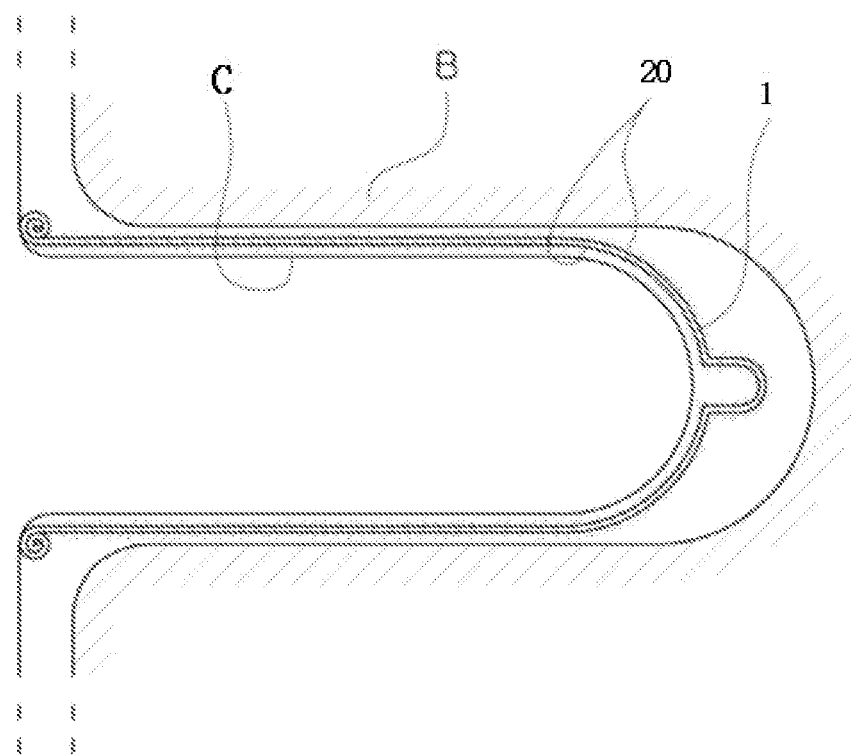
FIG. 9 illustrates an applied state of the condom of the present invention.

Furthermore, according to the present invention, the condom (1) may be accommodated in a sealed package (10) while the condom is immersed in lubricant jelly liquid (20), as illustrated in FIG. 8. By mixing a suitable amount of the vasodilators with the jelly liquid (20) accommodated in the package (10) of the condom (1), capillaries in a contact portion between the vagina and penis are locally enlarged in the use of the condom, thereby significantly increasing the sexual pleasure. Accordingly, an effect is obtained that female disease such as sexual anesthesia, colpoxerosis and dyspareunia can be effectively prevented and treated and male urological disease such as impotence, premature ejaculation, reduction of sexual pleasure etc. can be also treated, while reliable contraceptive function is exhibited, and in particular, a positive effect can be expected that the phenomenon of avoiding the condom is changed to preference of the use of the condom. Therefore, the present invention can be said to be a very useful invention.

The condom is accommodated in the sealed package (10) with the constricting ring at an opening side rolled up and the entire condom (1) is packed while it is sufficiently immersed in the lubricant jelly liquid (20) contained together. Therefore, when the condom is used, it is worn on the male penis with the jelly liquid (20) applied on the condom, and accordingly, the jelly liquid (20) contacts with outer circumferential surface (C) of the male penis and inner circumferential surface (B) of the female vagina and thus imparts good lubricity.

The present invention has a characteristic that the vasodilators is mixed with the jelly liquid (20) (lubricant) and when the jelly liquid (20) contacts with skin surface of the vagina in the use of the condom, the vasodilators enlarges capillary arterial vessels, thereby allowing the blood to smoothly circulate.

For the vasodilators mixed with the jelly liquid (20) of the present invention, various medical components may be selectively used whose safety has been clinically and widely verified.

In addition, citric acid sildenafil which is a main component of Viagra(trade name) that is a kind of anti-impotence drug, tadalafil which is a main component of cialis, udenafil which is a main component of zydena and the like may be mixed in liquid or powdery form.

a mixing amount of the vasodilators used may be appropriately adjusted in the range of 1 to 10 part by weight with respect to 100 part by weigh of the jelly liquid.

The vasodilators is mainly orally dosed. However, in the case of the present invention, if the vasodilators contacts with the female vaginal wall or circumferential skin of the male penis where peripheral blood vessels are developed, the solubility of the vasodilators is further increased by body temperature and components of drug liquid deeply penetrate inwards through skin cell membranes or pores to reach the capillary and then be absorbed into the blood by osmotic pressure phenomenon.

The vasodilators thus reaching the capillaries in the penis directly stimulates and enlarges the capillaries, and accordingly, the flow of blood, i.e. the circulation of capillary blood is promoted to be smooth; therefore, an effect is obtained that male erection power is increased and female sexual pleasure is remarkably enhanced.

That is, the increase of sexual pleasure provides a synergy effect of further promoting secretion of vaginal mucus by further stimulating female sexual nerves. Furthermore, the enlargement of blood vessels provides the man with a positive effect that it increases sexual desire to enhance the erection power and delays the ejaculation to prevent the premature ejaculation.

Therefore, using of the condom of the present invention provides an additional effect that the man can exhibit a good penis erection function even without taking the orally-dosed anti-impotence drug such as Viagra.

The present invention has been devised for the purpose of avoiding personal or social criticism and waste due to undesired pregnancy by improving a structure and functionality of male condom and thus further encouraging the public use of the condom, and thus has industrial applicability.

What is claimed is:

1. A condom with improved functionality, comprising a constricting ring provided at a rear portion of a main body of the condom, wherein a front glans penis portion of the main body of the condom is configured so that a space remains inside the front glans penis portion in order that a male glans penis is spaced apart from an inner surface of the front glans penis portion while the male glans penis is inserted and erected in the front glans penis portion, and moisturizing means with a lubricant moisturizing function is integrally coated on an outer surface of the main body of the condom, wherein the condom is accommodated in a sealed package while the condom is immersed in a lubricant jelly liquid, and wherein the lubricant jelly liquid includes vasodilators mixed therewith in a range of 1 to 10 part by weight with respect to 100 part by weigh of the lubricant jelly liquid, and is used as lubricant for the condom, and the vasodilators is selected from citric acid sildenafil, tadalafil and udenafil.

2. The condom with improved functionality according to claim 1, wherein the moisturizing means with the lubricant moisturizing function is further integrally coated on the inner surface of the front glans penis portion of the main body of the condom.

* * * * *